US009199954B2

(12) United States Patent
Kozlowski et al.

(10) Patent No.: US 9,199,954 B2
(45) Date of Patent: Dec. 1, 2015

(54) NON-RING HYDROXY SUBSTITUTED TAXANES AND METHODS FOR SYNTHESIZING THE SAME

(75) Inventors: Antoni Kozlowski, Huntsville, AL (US); Samuel P. McManus, Guntersville, AL (US)

(73) Assignee: Nektar Therapeutics, San Francisco, CA (US)

( * ) Notice: Subject to any disclaimer, the term of this patent is extended or adjusted under 35 U.S.C. 154(b) by 0 days.

(21) Appl. No.: 13/995,445

(22) PCT Filed: Dec. 22, 2011

(86) PCT No.: PCT/US2011/066778
§ 371 (c)(1),
(2), (4) Date: Oct. 10, 2013

(87) PCT Pub. No.: WO2012/088391
PCT Pub. Date: Jun. 28, 2012

(65) Prior Publication Data
US 2014/0024845 A1    Jan. 23, 2014

Related U.S. Application Data

(60) Provisional application No. 61/426,177, filed on Dec. 22, 2010.

(51) Int. Cl.
C07D 305/00 (2006.01)
C07D 305/14 (2006.01)
C07D 305/06 (2006.01)

(52) U.S. Cl.
CPC ............ *C07D 305/14* (2013.01); *C07D 305/06* (2013.01)

(58) Field of Classification Search
CPC .................................................. C07D 305/14
USPC ................................................. 549/510, 511
See application file for complete search history.

(56) References Cited

U.S. PATENT DOCUMENTS

| 5,294,637 | A | * | 3/1994 | Chen et al. ..................... 514/449 |
| 5,756,776 | A | * | 5/1998 | Bombardelli et al. ........ 549/510 |
| 5,847,170 | A | * | 12/1998 | Bouchard et al. ............. 549/510 |
| 5,914,311 | A | | 6/1999 | Barenholz et al. |
| 6,018,073 | A | | 1/2000 | Holton et al. |
| 6,124,482 | A | | 9/2000 | Ramadoss et al. |
| 6,649,778 | B1 | | 11/2003 | Zhao et al. |
| 7,186,851 | B2 | | 3/2007 | Baloglu |
| 2008/0262250 | A1 | | 10/2008 | Naidu |
| 2009/0069410 | A1 | | 3/2009 | Czarnik |
| 2013/0338216 | A1 | | 12/2013 | Kozlowski et al. |

FOREIGN PATENT DOCUMENTS

| CN | 101422613 | 5/2009 |
| EP | 2 108 368 | 10/2009 |
| WO | WO 90/10443 | 9/1990 |
| WO | WO 95/26967 | 10/1995 |
| WO | WO 2007/065869 | * 6/2007 ................ 549/510 |
| WO | WO 2008/066902 | 6/2008 |
| WO | WO 2010/019233 | 2/2010 |
| WO | WO 2012/088433 | 6/2012 |

OTHER PUBLICATIONS

Pulicani J-P et al., Tetrahedron Letters, 35 (52), 1994, 9717-9720.*
Naoyuki Harada et al., Heterocycles, 46, 1997, 241-258.*
Ojima I. et al., Tetrahedron, 52 (1), 1996, 209-224.*
Dutta et al., Bioorg. Med. Chem. Lett. 9 (23), 1999, 3277-3278.*
Lu et al., European J. Med. Chem., 44 (2), 2009, 482-491.*
Dumont, "Perspectives dans l'utilisation de molecules deuteriees en tant qu'agents therapeutiques," Revue IRE Tijdschrift, vol. 6, No. 4, pp. 2-10, (1982).
Foster, "Deuterium Isotope Effects in the Metabolism of Drugs and Xenobiotics: Implications for Drug Design," Advances in Drug Research, vol. 14, pp. 1-40, (1985).
Kushner, et al., "Pharmacological uses and perspectives of heavy water and deuterated compounds," Can. J. Physiol. Pharmacol., vol. 77, pp. 79-88, (1999).
Deutsch, et al, "Synthesis of Congeners and Prodrugs. 3. Water-Soluble Prodrugs of Taxol with Potent Antitumor Activity," J. Med. Chem., vol. 32, No. 4, pp. 788-792, (1989).
Fang, et al., "Synthesis and Antitumor Activity of C-2/C-10 Modified Analogues of Docetaxel," Chinese Chemical Letters, vol. 16, No. 1, pp. 38-40, (2005).
Greenwald, et al., "Synthesis, Isolation, and Characterization of 2'-Paclitaxel Glycinate: An Application of the Bsmoc Protecting Group," J. Org. Chem., vol. 68, No. 12, pp. 4894-4896, (2003).
Hodous, et al., "Enantioselective Staudinger Synthesis of β-Lactams Catalyzed by a Planar-Chiral Nucleophile," J. Am. Chem. Soc., vol. 124, No. 8, pp. 1578-1579, (2002).
Holton, et al., "Selective Protection of the C(7) and C(10) Hydroxyl Groups in 10-Deacetyl Baccatin III," Tetrahedron Letters, vol. 39, pp. 2883-2886, (1998).
Lee, et al., "Catalytic Asymmetric Staudinger Reactions to Form β-Lactams: An Unanticipated Dependence of Diastereoselectivity on the Choice of the Nitrogen Substituent," J. Am. Chem. Soc., vol. 127, No. 33, pp. 11586-11587, (2005).
Magri, et al., "Modified Taxols. 3. Preparation and Acylation of Baccatin III," J. Org. Chem., vol. 51, No. 16, pp. 3239-3242, (1986).
Mathew, et al., "Synthesis and Evaluation of Some Water-Soluble Prodrugs and Derivatives of Taxol with Antitumor Activity," J. Med. Chem., vol. 35, No. 1, pp. 145-151, (1992).
Pendri, et al., "Antitumor activity of paclitaxel-2'-glycinate conjugated to poly(ethylene glycol): a water-soluble prodrug," Anti-Cancer Drug Design, vol. 13, pp. 387-395, (1998).
Serrano-Wu, et al., "Mild deprotection of 2-(trimethylsilyl)ethyl esters," Tetrahedron Letters, vol. 42, pp. 8593-8595, (2001).
Sugahara, et al., "Paclitaxel Delivery Systems: The Use of Amino Acid Linkers in the Conjugation of Paclitaxel with Carboxymethyldextran to Create Prodrugs," Biol. Pharm. Bull., vol. 25, No. 5, pp. 632-641, (2002).

(Continued)

*Primary Examiner* — Andrew D Kosar
*Assistant Examiner* — Raymond Covington

(57) ABSTRACT

The invention relates to (among other things) non-ring hydroxy substituted taxanes and methods for synthesizing the same. The invention further relates to conjugating the non-ring hydroxyl substituted taxanes to a water-soluble, non-peptidic polymer.

8 Claims, No Drawings

(56) References Cited

OTHER PUBLICATIONS

Xiao, et al., "Design and Synthesis of a Taxoid Library Using Radiofrequency Encoded Combinatorial Chemistry," J. Org. Chem., vol. 62, No. 17, pp. 6029-6033, (1997).

Zhang, et al., "Chiral N-Heterocyclic Carbene Catalzyed Staudinger Reaction of Ketenes with Imines: Highly Enantioselective Synthesis of N-Boc β-Lactams," Organic Letters, vol. 10, No. 2, pp. 277-280, (2008).

PCT International Search Report and Written Opinion corresponding to PCT International Application No. PCT/US2011/066778 date of mailing Apr. 3, 2012.

PCT International Preliminary Report on Patentability corresponding to PCT International Application No. PCT/US2011/066778 date of mailing Jul. 4, 2013.

Enzon Pharmaceuticals, Macromolecular Engineering Technologies, 16 pages, (2004).

Nektar™—Transforming Therapeutics, Nektar Molecule Engineering: Polyethylene Glycol and Derivatives for Advanced PEGylation, 24 pages, Catalog—2003, (Jul. 2003).

Nektar™—Transforming Therapeutics, Nektar Advanced PEGylation: Polyethylene Glycol and Derivatives for Advanced PEGylation, 27 pages, Catalog—2004, (Jul. 2004).

Nektar™—Transforming Therapeutics, Nektar Advanced PEGylation: Polyethylene Glycol and Derivatives for Advanced PEGylation, 33 pages, (Catalog 2005-2006).

NOF Corporation, PEG Derivatives, Phospholipid and Drug Delivery Materials for Pharmaceuticals, 46 pages, Catalogue 2003—$1^{st}$, (Jan. 2003).

NOF Corporation, PEG Derivatives, Phospholipid and Drug Delivery Materials for Pharmaceuticals, 27 pages, Catalogue 2003—$2^{nd}$, (Mar. 2004).

NOF Corporation, PEG Derivatives, Phospholipids and Drug Delivery Materials for Pharmaceutical Products and Formulations, 60 pages, Catalogue Ver. 8, (Apr. 2006).

Polypure Products, PEG amines; PEG acids and amino acids; PEG thiols and disulfides; Biotins, 5 pages, (Apr. 2004).

Polypure Products, PEG amines; PEG acids and amino acids; PEG thiols and disulfides; Biotins, 5 pages, (Apr. 2005).

Quanta Biodesign, Labeling, Derivatization and Crosslinking Reagents for Biological and Related Materials with dPEG™, 38 pages, (Mar. 12, 2004).

Quanta Biodesign, Labeling, Modification and Crosslinking Reagents incorporating our unique monodispersed dPEG™ Technology, 31 pages, (Nov. 5, 2004).

Quanta Biodesign, Ltd., Leading innovator, producer and provider of monodisperse discrete PEG™ (dPEG™) derivatives, (Product Catalog), 26 pages, (Updated: Jul. 18, 2005).

Quanta Biodesign, Ltd., Leading innovator, producer and provider of monodisperse discrete PEG™ (dPEG™) derivatives, (Product Catalog), 26 pages, (Updated: Nov. 17, 2005).

Shearwater Polymers, Inc., Polyethylene Glycol Derivatives, 50 pages, Catalog—(Mar. 1995).

Shearwater Polymers, Inc., Polyethylene Glycol Derivatives, 55 pages, Catalog 1997-1998, (Jul. 1997).

Shearwater Polymers, Inc., Polyethylene Glycol and Derivatives: Functionalized Biocompatible Polymers for Research and Pharmaceuticals, 50 pages, Catalog—(Jan. 2000).

Shearwater Corporation, Polyethylene Glycol and Derivatives for Biomedical Applications, 20 pages, Catalog—(Jul. 2001).

* cited by examiner

NON-RING HYDROXY SUBSTITUTED TAXANES AND METHODS FOR SYNTHESIZING THE SAME

CROSS REFERENCE TO RELATED APPLICATIONS

This application is a 35 U.S.C. §371 application of International Application No. PCT/US2011/066778, filed Dec. 22, 2011, designating the United States, which claims the benefit of priority under 35 U.S.C. §119(e) to U.S. Provisional Patent Application Ser. No. 61/426,177 filed Dec. 22, 2010, the disclosures of which are incorporated herein by reference in their entireties.

FIELD OF THE INVENTION

This invention comprises (among other things) non-ring hydroxy substituted taxanes and methods for synthesizing the same. The compounds and methods described herein relate to and/or have application(s) in (among others) the fields of drug discovery, pharmacotherapy, and organic chemistry.

BACKGROUND OF THE INVENTION

Taxanes are chemically complex antineoplastic agents that were originally derived from the needles of the European yew tree. Often extremely potent, taxanes are notoriously insoluble in water. Efforts to attenuate the toxicities associated with taxanes, as well as attempts to improve their solubility, have focused on preparing conjugates of a water-soluble polymer covalently attached to a taxane. See, for example, WO 2010/019233.

Hydroxy groups on a drug represent useful points of attachment for a water-soluble polymer, and taxanes generally have several. The taxane drug, docetaxel, for example has four hydroxy groups, but only one of which—the "non-ring hydroxy"—is the preferred location at which a water-soluble polymer is attached.

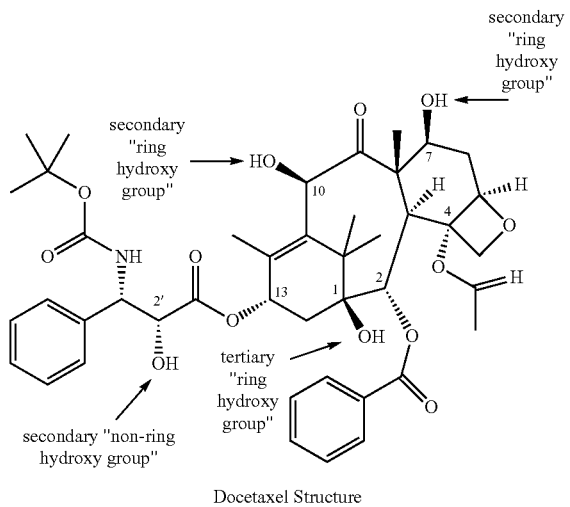

Docetaxel Structure

In one approach for preparing water-soluble conjugates of docetaxel, a water-soluble polymer reagent that forms covalent bonds with hydroxy groups is reacted under conjugation conditions with docetaxel. Although such an approach is useful, a mixture of water-soluble polymer-docetaxel conjugates results wherein one, two or more polymers may be attached at any combination of hydroxy groups, e.g., as illustrated in the structure below:

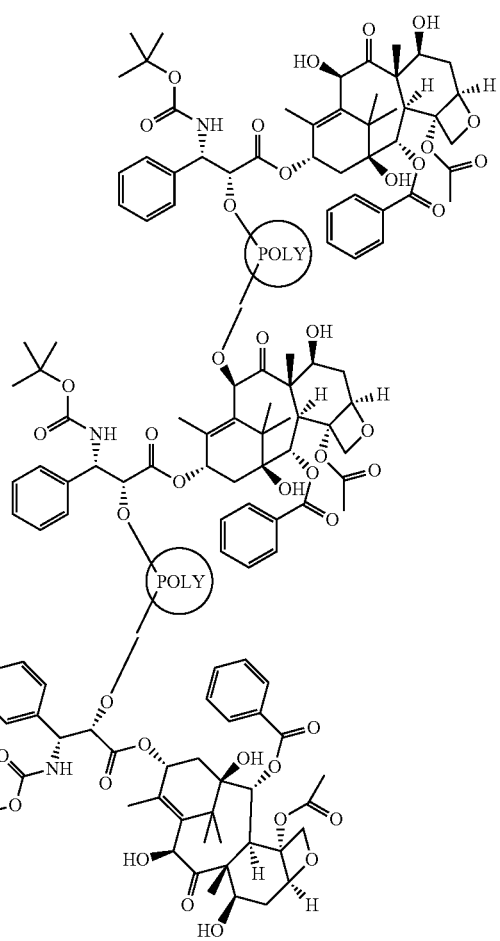

In order to avoid results such as those depicted above and to obtain the desired product, additional purification steps or the use of protecting groups may be required, thereby adding cost and complexity to the synthesis of these compounds.

In another approach, docetaxel may be functionalized at the desired non-ring hydroxy group to provide a substituted docetaxel bearing an alternative functional group (e.g., amine). Although the alternative functional group may allow for more specific conjugation (e.g., because the alternative functional group is not present anywhere else within the molecule), similar to the aforementioned drawback associated with the water-soluble polymer reagent attaching at a variety of hydroxy groups, functionalization of, for example, amines at hydroxy groups also results in a mixture of substituted hydroxyl groups. Particularly in the context of prodrug approaches, random modification of hydroxy groups will release a version of the drug that is likely to retain at least some of the modified forms of the hydroxy group (rather than the hydroxy group itself), wherein such modified forms of the drug may not have the desired activity.

The challenge associated with competition among the various hydroxy groups within docetaxel is shared among all taxanes for which conjugation to a water-soluble polymer is desired. Only in the case of those that have capped hydroxy groups at positions 7 and 10, e.g. cabazitaxel has methoxy groups, will competition be essentially nonexistent, as the tertiary hydroxy group at ring position 1 is much less reactive than any of the secondary hydroxy groups.

It would therefore be useful to have an approach and compounds that avoid this competition among the several hydroxy groups of taxanes.

The present invention seeks to address these and other needs in the art.

SUMMARY OF THE INVENTION

In one or more embodiments of the invention, a compound is provided, the compound encompassed by the formula:

Formula I

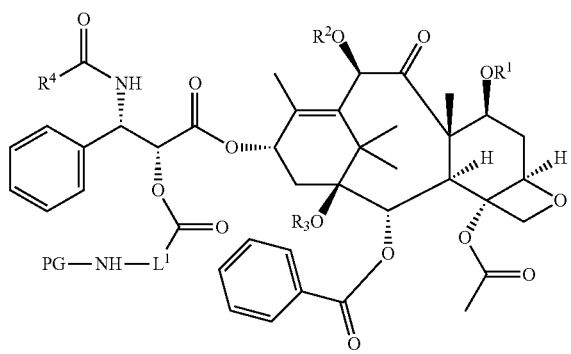

wherein:

$R^1$ is selected from the group consisting of H, a hydroxy protecting group, a $C_{1-6}$ organic radical, and a deuterated/fluorinated $C_{1-6}$ organic radical

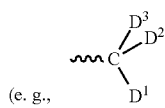

(e. g., and each of $D^1$, $D^2$ and $D^3$ is independently selected from the group consisting of H, F, D and $CF_3$);

$R^2$ is selected from the group consisting of H, a hydroxy protecting group, a $C_{1-6}$ organic radical, and a deuterated/fluorinated $C_{1-6}$ organic radical

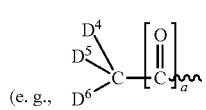

(e. g., and (a) is either zero or one and each of $D^4$, $D^5$ and $D^6$ is independently selected from the group consisting of H, F, D and $CF_3$);

$R^3$ is H or a hydroxy protecting group;

$R^4$ is $C_6H_5$— or

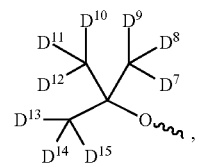

and each of $D^7$, $D^8$, $D^9$, $D^{10}$, $D^{11}$, $D^{12}$, $D^{13}$, $D^{14}$ and $D^{15}$ is independently selected from the group consisting of H, F and D;

$L^1$ is a non-reactive linker; and

PG is an amino protecting group.

In one or more embodiments of the invention, a method is provided, the method comprising the step of esterifying a baccatin III compound of Formula III, which compound is encompassed by the formula:

(baccatin III compound of Formula III)

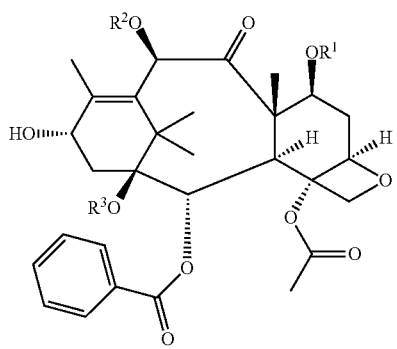

wherein:

$R^1$ is selected from the group consisting of H, a hydroxy protecting group, a $C_{1-6}$ organic radical, and a deuterated/fluorinated $C_{1-6}$ organic radical

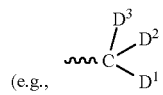

(e.g., and each of $D^1$, $D^2$ and $D^3$ is independently selected from the group consisting of H, F, D and $CF_3$);

$R^2$ is selected from the group consisting of H, a hydroxy protecting group, a $C_{1-6}$ organic radical, and a deuterated/fluorinated $C_{1-6}$ organic radical

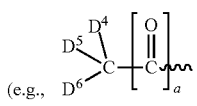

(e.g., and (a) is either zero or one and each of $D^4$, $D^5$ and $D^6$ is independently selected from the group consisting of H, F, D and $CF_3$); and $R^3$ is H or a hydroxy protecting group, with an ester linkage-providing compound of Formula II, which compound is encompassed by the formula:

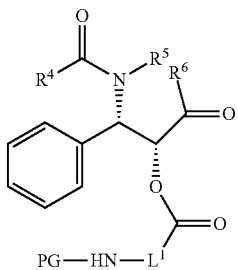

(Formula II)

wherein:

$R^4$ is $C_6H_5$— or

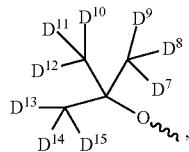

and each of $D^7$, $D^8$, $D^9$, $D^{10}$, $D^{11}$, $D^{12}$, $D^{13}$, $D^{14}$ and $D^{15}$ is independently selected from the group consisting of H, F and D;

$L^1$ is a nonreactive linker;

PG is an amino protecting group; and either: (i) $R^5$ is H and $R^6$ is —OH; or (ii) $R^5$ and $R^6$ represent a single covalent bond (formed from groups that participate in a process where a single covalent bond is formed) between the nitrogen to which $R^5$ is attached and the carbonyl carbon to which $R^6$ is attached, which method provides compounds encompassed by Formula I.

Additional embodiments of the present compounds, compositions, methods, and the like will be apparent from the following description, examples and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present invention. Additional aspects and advantages of the present invention are set forth in the following description and claims.

DETAILED DESCRIPTION OF THE INVENTION

In describing and claiming the present invention, the following terminology will be used in accordance with the definitions described below.

As used in this specification, the singular forms "a," "an," and "the" include plural referents unless the context clearly dictates otherwise.

When reference is made to the atom "D" (as in $D^1$ "is selected from the group consisting of H, F and D"), it shall be understood to encompass both deuterium and tritium, and the specification encompasses instances where D is deuterium and instances where D is tritium.

The term "protecting group" refers to the presence of a moiety (i.e., the protecting group) that prevents or blocks reaction of a particular chemically reactive functional group in a molecule under certain reaction conditions. The protecting group will vary depending upon the type of chemically reactive group being protected as well as the reaction conditions to be employed and the presence of additional reactive or protecting groups in the molecule, if any. Protecting groups known in the art can be found in, for example, Greene et al., "Protective Groups in Organic Synthesis," $3^{rd}$ Edition, John Wiley and Sons, Inc., New York, 1999.

The term "amino protecting group" means a protecting group suitable for preventing undesired reactions at an amino group. Representative amino protecting groups include, but are not limited to, carbobenzyloxy (Cbz), p-methoxybenzyl carbonyl (Moz, MeOZ), tert-butyloxycarbonyl (BOC or t-BOC), 9-fluorenylmethyloxycarbonyl (FMOC and similar derivatives), acetyl (Ac), benzoyl (Bz), benzyl (Bn), p-methoxybenzyl (PMB), 3,4-dimethoxybenzyl (DMPM), p-methoxyphenyl (PMP), and sulfonamides, e.g., such as tosyl (Ts). Amine protecting groups in this application will vary with the procedure being carried out and one of ordinary skill in the art can select (based on routine experimental and/or with reference to the relevant literature, in view of the disclosure provided herein) the appropriate protecting group that avoids complications that would exist if the amine group is either unprotected or improperly protected.

The term "hydroxy protecting group" means a protecting group suitable for preventing undesirable reactions at a hydroxy group. Representative hydroxy protecting groups include, but are not limited to, acetyl (Ac), formyl, benzoyl (Bz), benzyl (Bn, Bnl), benzyloxymethyl (BOM), p-methoxybenzyl (PMB), 9-fluorenylmethyl (Fm), diphenylmethyl (DPM), β-methoxyethoxymethyl ether (MEM), dimethoxytrityl [bis-(4-methoxyphenyl)phenylmethyl, DMT], methoxymethyl ether (MOM), methoxytrityl [(4-methoxyphenyl) diphenylmethyl, MMT], p-methoxybenzyl ether (PMB), methylthiomethyl ether, pivaloyl (Piv), tetrahydropyranyl (THP), trityl (triphenylmethyl, Tr), carbobenzyloxy (Cbz, and similar carbobenzyloxy derivatives), silyl ethers (e.g, trimethylsilyl (TMS), triethylsilyl (TES), tert-butyldimethylsilyl (TBDMS), tert-butyldimethylsilyloxymethyl (TOM), and triisopropylsilyl (TIPS) ethers), methyl ethers, and ethoxyethyl ethers. Protecting groups for hydroxy groups in this application will vary with the procedure being carried out and one of ordinary skill in the art can select (based on routine experimental and/or with reference to the relevant literature, in view of the disclosure provided herein) the appropriate protecting group that avoids complications that would exist if the hydroxy group is either unprotected or improperly protected.

The term nonreactive linker implies a series of atoms bonded together such that the groups attached to the nonreactive linker are separated. In some instances, the nonreactive linker will prevent interference and provide additional properties such as greater water solubility or insolubility to the molecule in which the linker is contained. Nonreactive in this context means that, under pH conditions of approximately 3-12 or in the presence of modestly active nucleophiles or electrophiles, the linker will not be chemically changed. Preferred nonreactive linkers for this application include alkylene groups such as —$CR_2$—, —$CR_2CR_2$—, etc. up to a chain of approximately 10 carbons, wherein each R is independently H, lower alkyl, or arylalkyl and including two or more R group connecting to produce cyclic chain entities; alkyleneoxy oligomers such as —$(CR'_2CR'_2O)_n$—, where R' is independently H or $CH_3$ and n=2 to 10; more complex combination linkers such as those with alkyleneoxy oligomers in between alkylene-like end components, such as —$(CR_2)_x$—$(CR'_2CR'_2O)_n$—$(CR_2)_y$— where n, R and R' are as defined above and x and y are independently 0 to 6. In one or more embodiments, the nonreactive linker lacks a carbonyl.

"Substantially" or "essentially" means nearly totally or completely, for instance, 95% or greater, more preferably 97% or greater, still more preferably 98% or greater, even more preferably 99% or greater, yet still more preferably 99.9% or greater, with 99.99% or greater being most preferred of some given quantity.

A basic reactant or an acidic reactant described herein include neutral, charged, and any corresponding salt forms thereof.

Any compound described herein also can be provided in salt form (e.g., a pharmaceutically acceptable salt, such as the hydrochloride salt).

"Optional" or "optionally" means that the subsequently described circumstance may but need not necessarily occur, so that the description includes instances where the circumstance occurs and instances where it does not.

As indicated above, the present invention is directed to (among other things) compounds encompassed by Formula I,

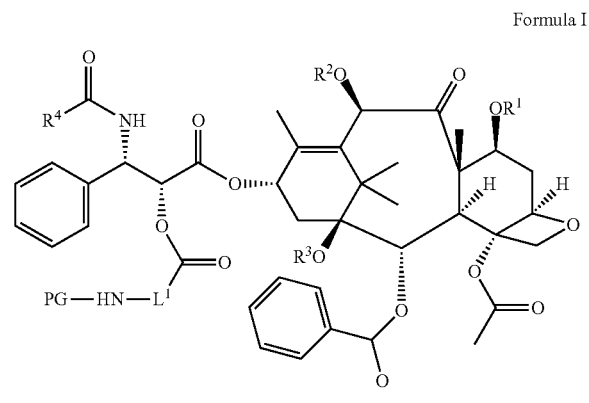

Formula I wherein:

$R^1$ is selected from the group consisting of H, a hydroxy protecting group, a $C_{1-6}$ organic radical, and a deuterated/fluorinated $C_{1-6}$ organic radical

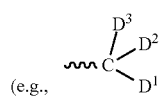

(e.g., and each of $D^1$, $D^2$ and $D^3$ is independently selected from the group consisting of H, F, D and $CF_3$);

$R^2$ is selected from the group consisting of H, a hydroxy protecting group, a $C_{1-6}$ organic radical, and a deuterated/fluorinated $C_{1-6}$ organic radical

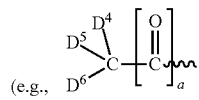

(e.g., and (a) is either zero or one and each of $D^4$, $D^5$ and $D^6$ is independently selected from the group consisting of H, F, D and $CF_3$);

$R^3$ is H or a hydroxy protecting group;

$R^4$ is $C_6H_5$— or

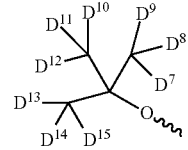

and each of $D^7$, $D^8$, $D^9$, $D^{10}$, $D^{11}$, $D^{12}$, $D^{13}$, $D^{14}$ and $D^{15}$ is independently selected from the group consisting of H, F and D;

$L^1$ is a non-reactive linker; and

PG is an amino protecting group.

In one or more embodiments, the invention is directed to a method of preparing compounds encompassed by Formula I, wherein the method comprises the step of esterifying a baccatin III compound of Formula III with an ester linkage-providing compound of Formula II to thereby result in a compound encompassed by Formula I. Compounds of Formula I are useful for, among other things, as intermediates for subsequent conjugation reactions between a compound of Formula I and a water-soluble, non-peptidic polymer.

With respect to the baccatin III compounds of Formula III, such compounds can be obtained from commercial sources and/or obtained synthetically. For example, the compound 10-deacetylbaccatin III can be isolated in accordance with the process described in U.S. Pat. No. 6,124,482.

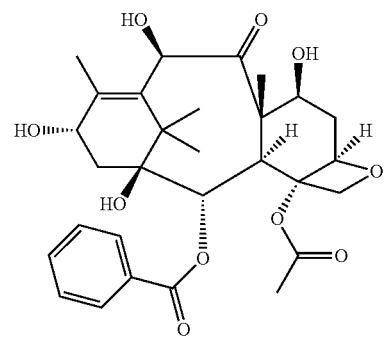

10-deacetylbaccatin III

Baccatin III can be obtained according to the process described in Magris et al. (1986) *Journal of Organic Chemistry* 51:3239-3242 and can also be obtained from Jinan Great Chemical Industry Co., Ltd (Shandong, China).

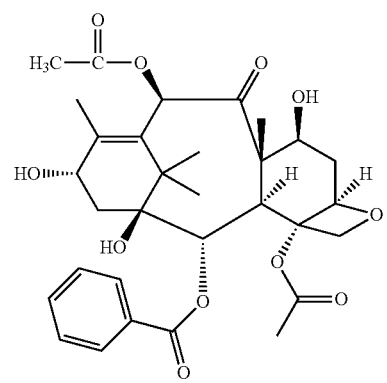

Baccatin III 7,10-Dimethoxy versions of 10-deacetylbaccitin III can be prepared synthetically using KH, CH₃I in the presence of THF, as shown below.

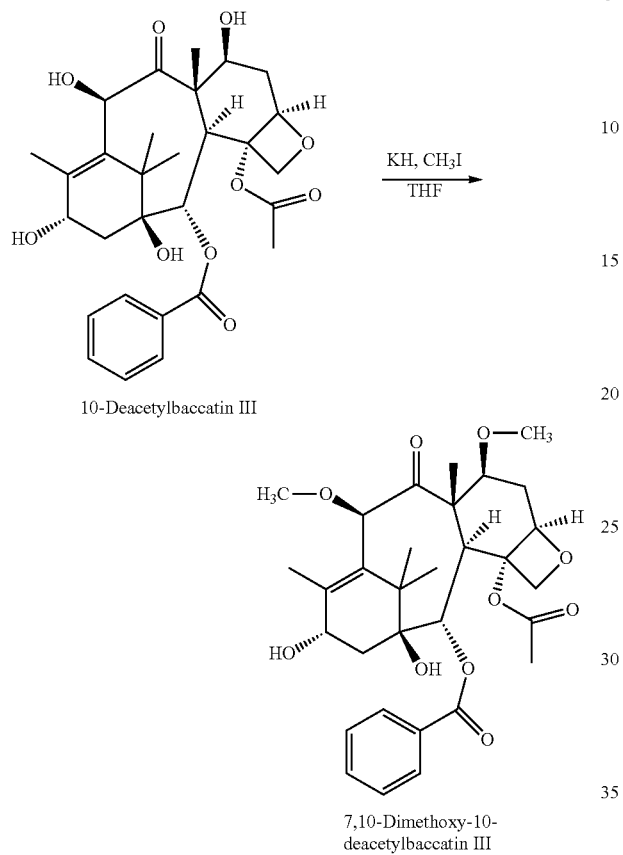

10-Deacetylbaccatin III 7,10-Dimethoxy-10-deacetylbaccatin III

Other embodiments of baccatin III compounds of Formula III can be prepared from baccatin III, 10-deacetylbaccatin III and 7,10-dimethoxy-10-deacetylbaccatin III. For example, protected forms of baccatin III, 10-deacetylbaccatin III and 7,10-dimethoxy-10-deacetylbaccatin III can be prepared using art-known protecting approaches. For example, compounds having hydroxy groups corresponding to $R^1$ and/or $R^2$ of Formula III can be protected using approaches described in U.S. Pat. Nos. 5,914,311 and 7,186,851, in WO 95/26967 and in Holton et al. (1998) *Tetrahedron Letters* 39:2883-2886.

In addition, $C_{1-6}$ alkyl, deuterated and/or fluorinated forms of baccatin III, 10-deacetylbaccatin III and 7,10-dimethoxy-10-deacetylbaccatin III can be prepared. For example, U.S. Provisional Patent Application No. 61/426,202, filed on Dec. 22, 2010, and entitled "Deuterated and/or Fluorinated Taxane Derivatives" and the corresponding international application of the same title filed on Dec. 22, 2011, that claims priority thereto describe deuterated and/or fluorinated versions of baccatin III compounds of Formula III; in addition, other deuterated and/or fluorinated versions of baccatin III compounds of Formula III can be prepared in accordance with the approaches described in this application.

The ester linkage-providing compound of Formula II can be obtained by synthesis beginning with readily available materials.

In a first exemplary approach for making an ester linkage-providing compound of Formula II, (2R,3S)3-phenylisoserine as a silicon protected ester is converted into a t-BOC protected amine hydroxy ester using t-butylchloroformate and an appropriate base under very mild conditions. In addition, "reagent a" shown below can be used with the (2R,3S) 3-phenylisoserine as a silicon protected ester into a t-BOC protected amine hydroxy ester.

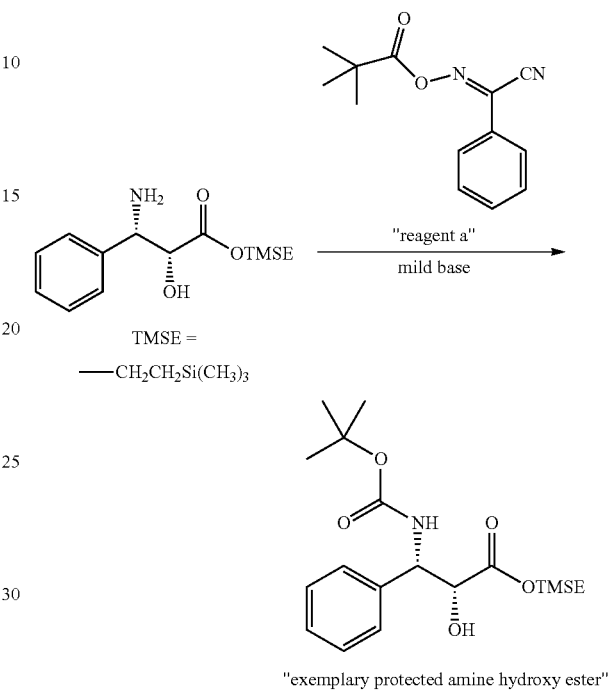

TMSE = —CH₂CH₂Si(CH₃)₃

"exemplary protected amine hydroxy ester"

No matter which specific approach is used to prepare the protected amine hydroxy ester (and the invention is not limited in this regard), the protected amine hydroxy ester is isolated and purified using known techniques. Then, a previously prepared nonreactive linker containing a protected terminal amine group (e.g., a tetraethylene glycol linker terminated at the reactive end with a lactic acid component, as shown immediately below) is coupled with the hydroxy ester using a condensing agent. Thereafter, optionally, the carboxylic acid-protecting group can be cleaved away using appropriate fluoride ion methods or using other mild methods such as described in Wu et al. (2001) *Tetrahedron Letters* 42: 8593-8595 and references therein.

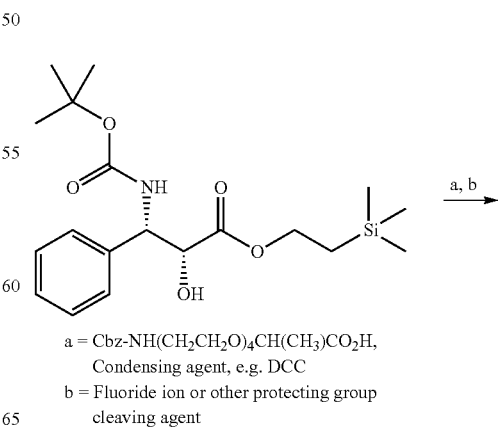

a = Cbz-NH(CH₂CH₂O)₄CH(CH₃)CO₂H,
   Condensing agent, e.g. DCC
b = Fluoride ion or other protecting group
   cleaving agent -continued In a second exemplary approach for making ester linkage-providing compounds of Formula II, a beta-lactam is employed. Schematically, the second approach is provided immediately below and starts with the formation of a beta lactam via reaction of a benzylimine with "reagent b", followed by attachment at the unprotected amine of the thus formed beta lactam to provide ~C(O)—R⁴ substituent of Formula II (shown as the tert-butyl ester in the schematic below).

"reagent b"
(where PG and L¹ are as defined with respect to Formula II)

Exemplary compounds encompassed within Formula II
(where PG and L¹ are as defined with respect to Formula II)

Techniques described in Fang et al. (2005) *Chinese Chem. Letters*, 16:38-40, U.S. Patent Application Publication No. 2008/0262250, Zhang et al. (2008) *Org. Lett.*, 10:277-280, Lee et al. (2005) *J. Am. Chem. Soc.*, 127:11586-11587, and Hodous et al. (2002) *J. Am. Chem. Soc.*, 124:1578-1579 can be adapted in this second exemplary approach.

Having obtained a baccatin III compound of Formula III and an ester linkage-providing compound of Formula II, the step of esterifying a baccatin III compound of Formula III will be described. The step of esterifying a baccatin III of compound III can occur by any number of ways and the invention is not limited in this regard.

In a first exemplary approach, the baccatin III compound of Formula III can be esterified via a condensation reaction with the use of a condensing agent. In this approach, a carboxylic acid-bearing version of the ester linkage-providing compound of Formula II, shown below as Formula IIa, is used.

(Formula IIa)

wherein:

$R^4$ is $C_6H_5$— or and each of $D^7$, $D^8$, $D^9$, $D^{10}$, $D^{11}$, $D^{12}$, $D^{13}$, $D^{14}$ and $D^{15}$ is independently selected from the group consisting of H, F, D and $CF_3$;

$L^1$ is a nonreactive linker;

PG is an amino protecting group.

Esterifying the non-ring hydroxy-bearing baccatin III compound of Formula III with the carboxylic acid-bearing compound of Formula IIa can be represented as shown in the schematic below.

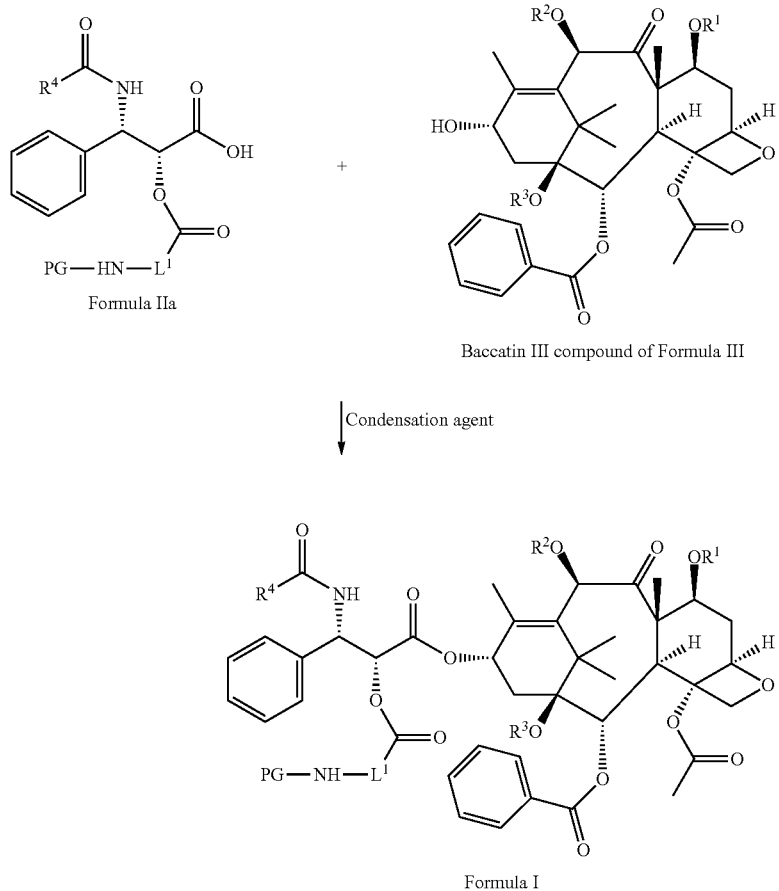

Formula IIa

Baccatin III compound of Formula III

Condensation agent

Formula I wherein (for all variables in the above schematic):

$R^1$ is selected from the group consisting of H, a hydroxy protecting group, a $C_{1-6}$

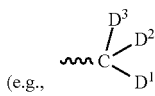

(e.g., )

organic radical, and a deuterated/fluorinated $C_{1-6}$ organic radical and each of $D^1$, $D^2$ and $D^3$ is independently selected from the group consisting of H, F, D and $CF_3$);

$R^2$ is selected from the group consisting of H, a hydroxy protecting group, a $C_{1-6}$ organic radical, and a deuterated/fluorinated $C_{1-6}$ organic radical

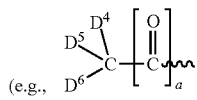

(e.g., )

(a) is either zero or one and each of $D^4$, $D^5$ and $D^6$ is independently selected from the group consisting of H, F, D and $CF_3$;

$R^3$ is H or a hydroxy protecting group;

$R^4$ is $C_6H_5$— or

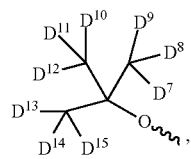

and each of $D^7$, $D^8$, $D^9$, $D^{10}$, $D^{11}$, $D^{12}$, $D^{13}$, $D^{14}$ and $D^{15}$ is independently selected from the group consisting of H, F, D and $CF_3$;

$L^1$ is a nonreactive linker; and

PG is an amino protecting group.

In carrying out the esterification step using a condensation reaction with the use of a condensation agent, the condensation agent (also known as an activation agent) is selected from those substances known in the art to cause carboxylic acids and alcohols to condense to form esters. Exemplary condensation agents are dehydrating substances such as alkyl carbodiimides or triarylphosphites that are consumed during the process. Specifically, dicyclohexylcarbodiimide (DCC), diisopropylcarbodiimide (DIC), and triphenylphosphite (TPP) are preferred condensation agents. Some of these agents are used with a catalyst or co-agent.

Other catalytic condensation reactions, such as Fischer esterification, are less preferred because the typical condensations for such processes are too severe for a molecule like Baccatin III, which has acid-sensitive groups. Thus, in some instances the catalytic condensation reactions, such as Fischer esterification, are not used as part of the synthetic method described herein.

With respect to solvents, the esterification step using a condensation reaction with the use of a condensation agent takes place in an appropriate solvent. One of ordinary skill in the art can determine whether a given solvent is appropriate for the esterification step being employed. Typically, however, the solvent will be an aprotic nonreactive solvent. Non-limiting examples of nonpolar solvents include hydrocarbons like methylcyclohexane, xylene and toluene, ethers like dioxane, diglyme, and tetrahydrofuran (THF), certain nitriles like acetonitrile, halohydrocarbons like methylene chloride and certain aprotic dipolar solvents like dimethylformamide (DMF). Mixtures of two solvents may be used to obtain the appropriate solubility of components. Also, one may also choose a solvent wherein the product of the condensing agent, i.e., dicyclohexylurea, in the case of DCC, will precipitate out and facilitate reaction workup.

Because condensation agents like DCC activate the carboxyl group by forming an intermediate that is very reactive, a structure of Formula II activated with the exemplary condensation agent DCC is shown below. Also shown below is a reactive beta lactam and an activated succinimidyl ester. These activated species are then very reactive toward the deprotonated hydroxy group at C-13 in the condensation reaction. (For reference to the location of "C-13" in docetaxel, see the "Docetaxel Structure" provided above where "C-13" is indicated; in view of the description herein, corresponding "C-13" locations within the other structures provided herein will be apparent).

Formula II activated by DCC

Formula IIb

Formula IIc

Other options for conducting this condensation reaction involve previously prepared activated forms of the carboxylic acid that can be isolated and optionally purified. Thus, Formula Jib represents a beta-lactam form that is highly activated for ring-opening condensation and Formula IIc is an activated carboxylic acid, N-hydroxysuccidimidyl (NHS) ester. In embodiments further described below, these two forms will be illustrated, although other activated forms can be used and the present disclosure encompasses embodiments using these other activated forms.

In a second exemplary approach for carrying out the step of esterifying a baccatin III of compound III, the baccatin III compound of Formula III can be esterified in a condensation reaction using a beta lactam version of Formula II. In this approach, a beta lactam-bearing version of the ester linkage-providing compound of Formula II, shown below as Formula IIb, is used.

(Formula IIb)

wherein:
$R^4$ is $C_5H_6$— or and each of $D^7$, $D^8$, $D^9$, $D^{10}$, $D^{11}$, $D^{12}$, $D^{13}$, $D^{14}$ and $D^{15}$ is independently selected from the group consisting of H, F and D;

$L^1$ is a nonreactive linker; and

PG is an amino protecting group.

Esterifying the non-ring hydroxy-bearing baccatin III compound of Formula III with the beta lactam-bearing compound of Formula IIa in the presence of a drying agent can be represented as shown in the schematic below.

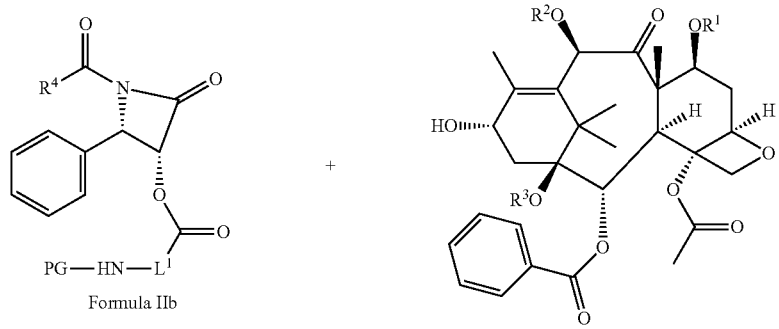

Formula IIb

+

Baccatin III compound of Formula III

↓

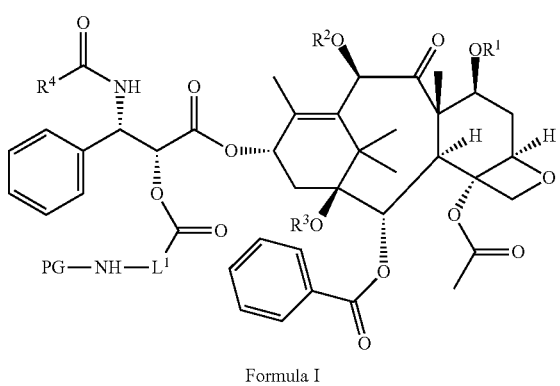

Formula I wherein (for all variables in the above schematic):

$R^1$ is selected from the group consisting of H, a hydroxy protecting group, a $C_{1-6}$ organic radical, and a deuterated/fluorinated $C_{1-6}$ organic radical (e.g., 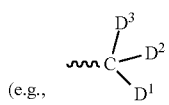)

and each of $D^1$, $D^2$ and $D^3$ is independently selected from the group consisting of H, F, D and $CF_3$);

$R^2$ is selected from the group consisting of H, a hydroxy protecting group, a $C_{1-6}$ (e.g., 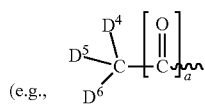)

organic radical, and a deuterated/fluorinated $C_{1-6}$ organic radical and (a) is either zero or one and each of $D^4$, $D^5$ and $D^6$ is independently selected from the group consisting of H, F, D and $CF_3$);

$R^3$ is H or a hydroxy protecting group;

$R^4$ is $C_6H_5$— or

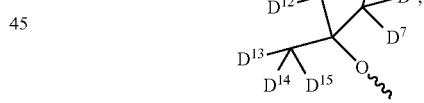

and each of $D^7$, $D^8$, $D^9$, $D^{10}$, $D^{11}$, $D^{12}$, $D^{13}$, $D^{14}$ and $D^{15}$ is independently selected from the group consisting of H, F and D;

$L^1$ is a nonreactive linker; and

PG is an amino protecting group.

In carrying out the esterification step using a beta lactam, the baccatin III compound of Formula III is first protected with a hydroxy protecting groups such that hydroxy groups are protected except for the one at C-13. The baccatin III compound of Formula III derivative so protected is thereafter dissolved in an appropriate nonreactive solvent, such as THF, diglyme, toluene and the like, or mixtures of such solvents. Then, at low temperature (i.e., approximately −40° C. or lower and preferably −78° C.), a solution or slurry of a poorly nucleophilic deprotonating base, such as n-butyl lithium, sodium hydride, potassium t-butoxide, or the like, is added with stirring. After an appropriate time, generally about 30 minutes, a dry solution of a compound of Formula IIb is dissolved in the reaction solvent by adding dropwise with stirring and the reaction is allowed to proceed to completion as the reaction temperature is slowly raised to about 0° C. After about an hour, the reaction can be quenched with a cooled solution of a mild acid, i.e., acetic acid, in the reaction solvent. The reaction mixture can then be processed to recover the product and purify it by recrystallization or another appropriate method such as chromatography or biotage. One of ordinary skill in the art can select solvent, reaction conditions, temperatures, workup conditions, purification methods by, for example, trialing small scale reactions. A schematic demonstrating this approach if provided immediately below.

In yet another embodiment, activated esters such as those of Formula IIc can be utilized in condensation processes to provide compounds of Formula I. Activated esters of Formula IIc have various leaving groups other than N-hydroxysuccinimide, which is a preferred leaving group. For example, other leaving groups that are acceptable are p-nitrophenolate, bromide, 1-hydroxybenzotriazole (HOBT), and many others known in the art. Having obtained an activated ester of Formula IIc (or other appropriate activated ester corresponding to the compounds of Formula IIc), a typical condensation process is described and is shown schematically below.

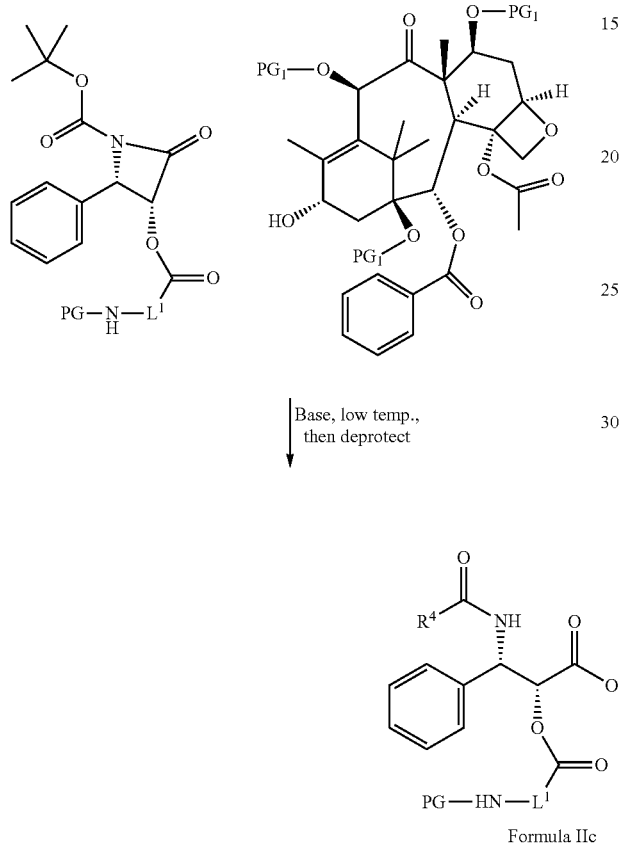

In this process, the baccatin III compound of Formula III will have all (or substantially all) hydroxy groups protected except for the one at C-13. Then, the protected baccatin III compound of Formula III so formed is thereafter dissolved in an appropriate nonreactive solvent, such as THF, diglyme, toluene and the like, or mixtures of solvents. Then, at low temperature (i.e., approximately −40° C. or lower and preferably −78° C.) a solution or slurry of a poorly nucleophilic deprotonating base, such as n-butyl lithium, sodium hydride, potassium t-butoxide, or the like, is added with stirring. After an appropriate time, generally about 30 minutes, a dry solution of the activated ester of Formula IIc (or other appropriate activated ester corresponding to the compounds of Formula IIc), is dissolved in the reaction solvent by adding dropwise with stirring and the reaction is allowed to proceed to completion as the reaction temperature is slowly raised to about 0° C. After about an hour the reaction can be quenched with a cooled solution of a mild acid, i.e., acetic acid, in the reaction solvent. The reaction mixture can then be processed to recover the product and purify it by recrystallization or another appropriate method such as chromatography or biotage.

Having obtained compounds of Formula I, in one or more embodiments of the invention, the method includes the optional step(s) of deprotecting one or more of any hydroxy protecting groups, deprotecting any amino protecting groups, or deprotecting any hydroxyl protecting groups and the amino protecting groups (in either order or simultaneously). The optional deprotecting step(s), when carried out, will depend on the protecting group(s) present. One of ordinary skill in the art, upon review of the present application, will be able to determine the appropriate conditions to deprotect the desired hydroxy protecting group(s) and/or amino protecting groups.

Briefly, however, in one or more embodiments of the invention, the method includes the optional step of removing any hydroxy protecting groups associated with compounds encompassed by Formula I (i.e., when any of $R^1$, $R^2$ and $R^3$ in Formula III are defined as a hydroxy protecting group). Hydroxy protecting groups can be removed by any suitable method and the invention is not limited in this regard. Exemplary approaches for removing hydroxy protecting groups include treatment with an acid (e.g., for acetyl, benzyl, β-methoxyethoxymethyl ether, dimethoxytrityl, methoxymethyl ether, methoxytrityl, p-methoxybenzyl ether, methylthiomethyl ether, pivaloyl, tetrahydropyranyl, trityl, silyl ether, and ethoxyethyl ether hydroxy protecting groups), treatment with a base (e.g., for acetyl, benzoyl and pivaloyl hydroxy protecting groups), hydrogenolysis (e.g., for benzyl, benzyloxymethyl, methoxytrityl, p-methoxybenzyl ether and trityl hydroxy protecting groups), oxidation (e.g., for p-methoxybenzyl ether hydroxy protecting group), and treatment with $BBr_3$ is methylene chloride (e.g., for methyl ether hydroxy protecting group). When protecting groups associated with compounds encompassed by Formula I are removed, standard approaches are used to avoid affecting any remaining functional groups. The disclosure provided herein is instructive in this respect.

In addition, in one or more embodiments of the invention, the method includes the optional step of removing any amino protecting groups associated with compounds encompassed by Formula I (i.e., when PG in Formula III is defined as an amino protecting group). Amino protecting groups can be removed by any suitable method and the invention is not limited in this regard. Exemplary approaches for removing amino protecting groups include treatment with an acid (e.g., for tert-butyloxycarbonyl and tosyl amino protecting groups), hydrogenolysis (e.g., for carbobenzyloxy, p-methoxybenzyl carbonyl, benzyl, p-methoxybenzyl, and 3,4-dimethoxybenzyl amino protecting groups), treatment with a base (e.g., for 9-fluorenylmethyloxycarbonyl, acetyl, and benzoyl amino protecting groups), and treatment with ammonium cerium nitrate (e.g., for p-methoxyphenyl amino protecting group). When protecting groups for amino groups are removed, standard approaches are used to avoid affecting any remaining functional groups. The disclosure provided herein is instructive in this respect.

The methods described herein provide compounds encompassed by Formula I. Exemplary compounds of Formula I include those selected from the group consisting of:

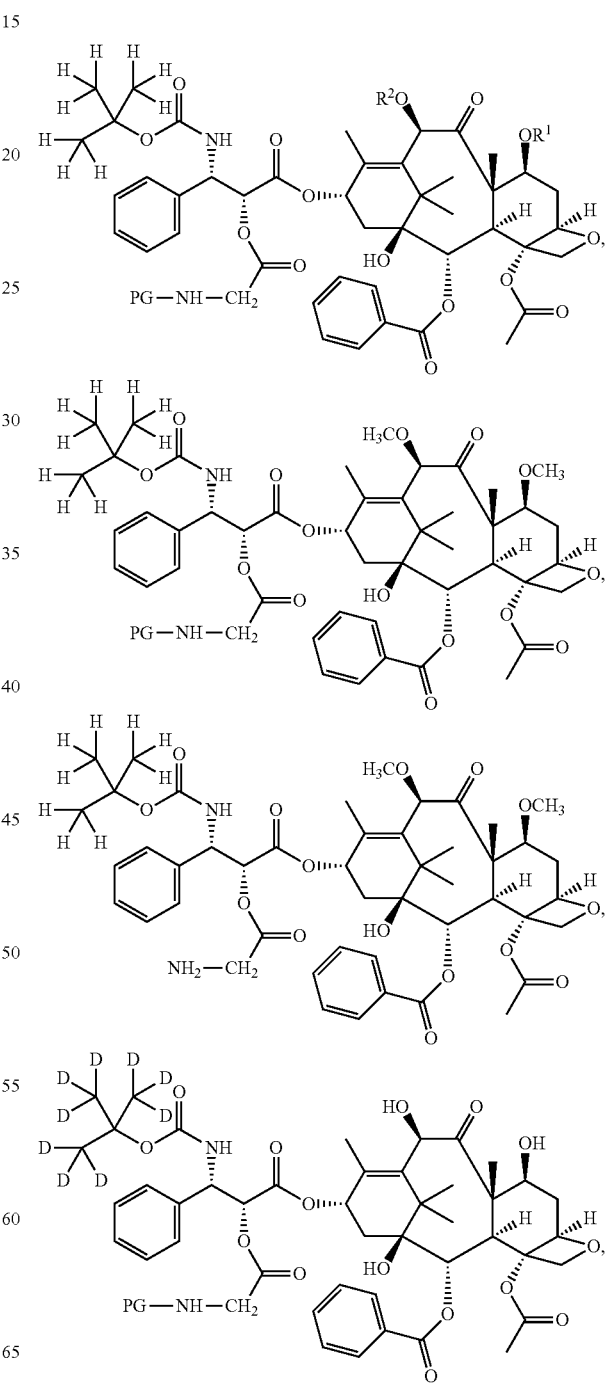

23
-continued
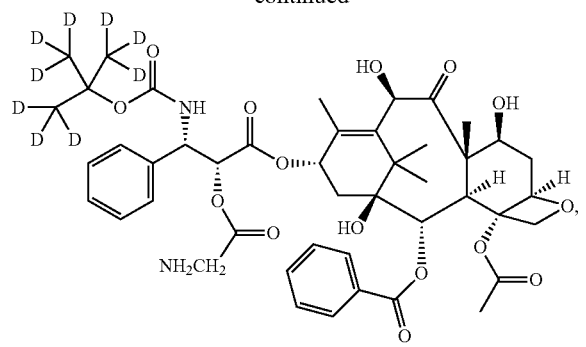
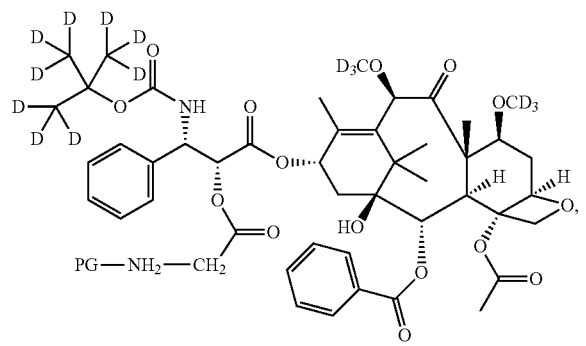
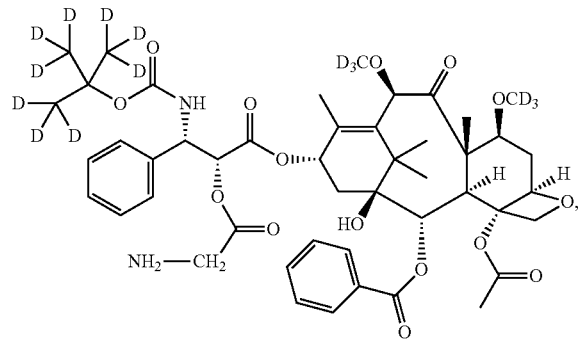
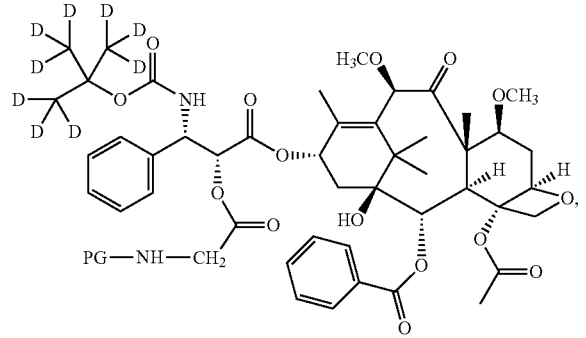
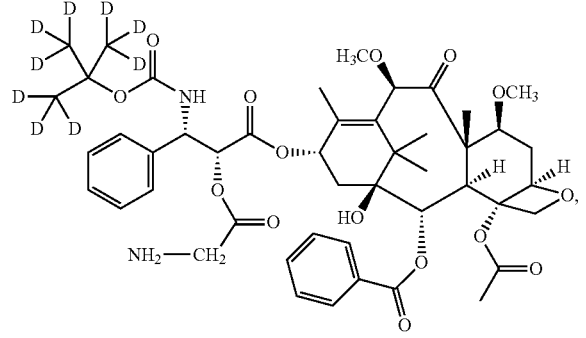
24
-continued
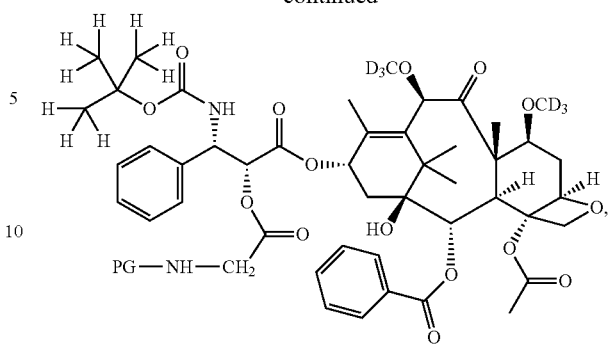
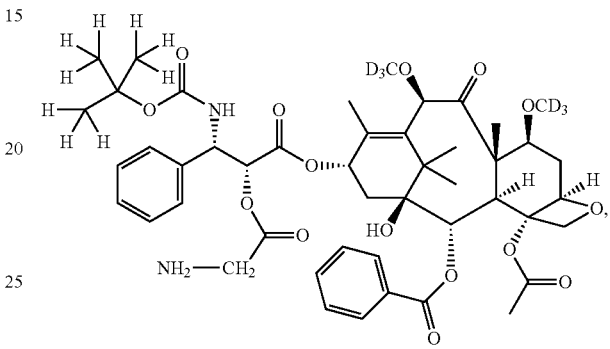
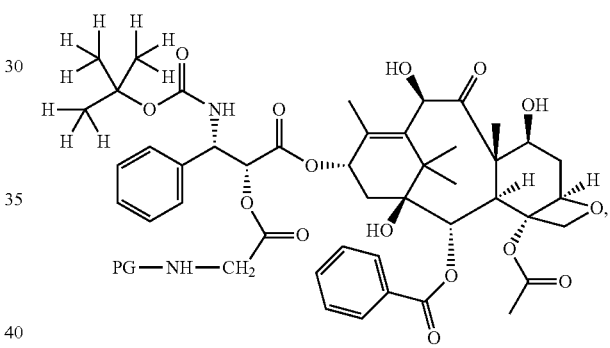
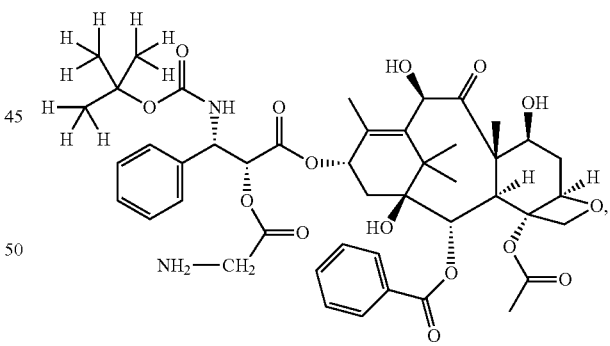
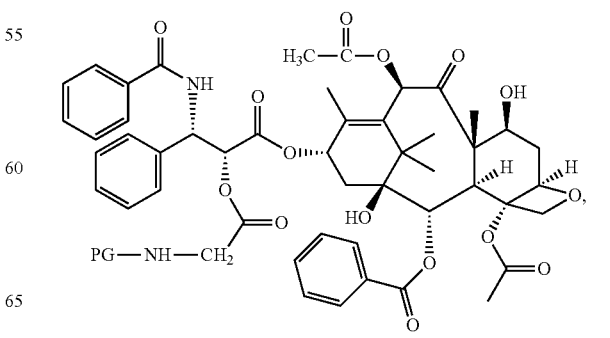

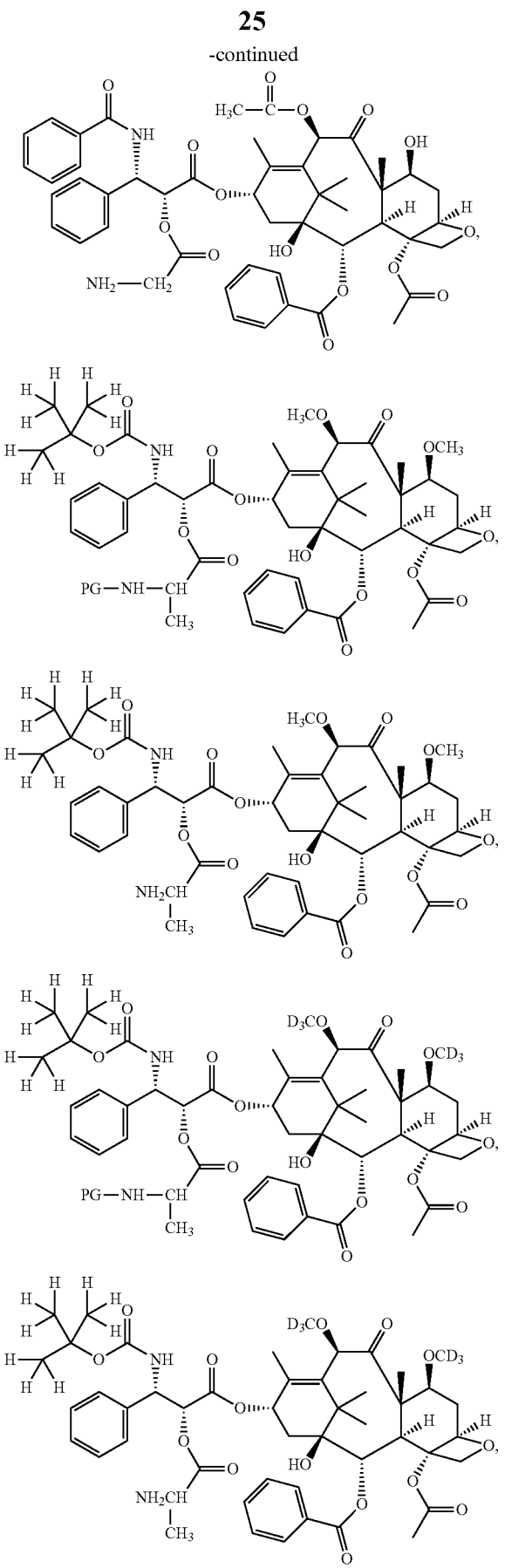

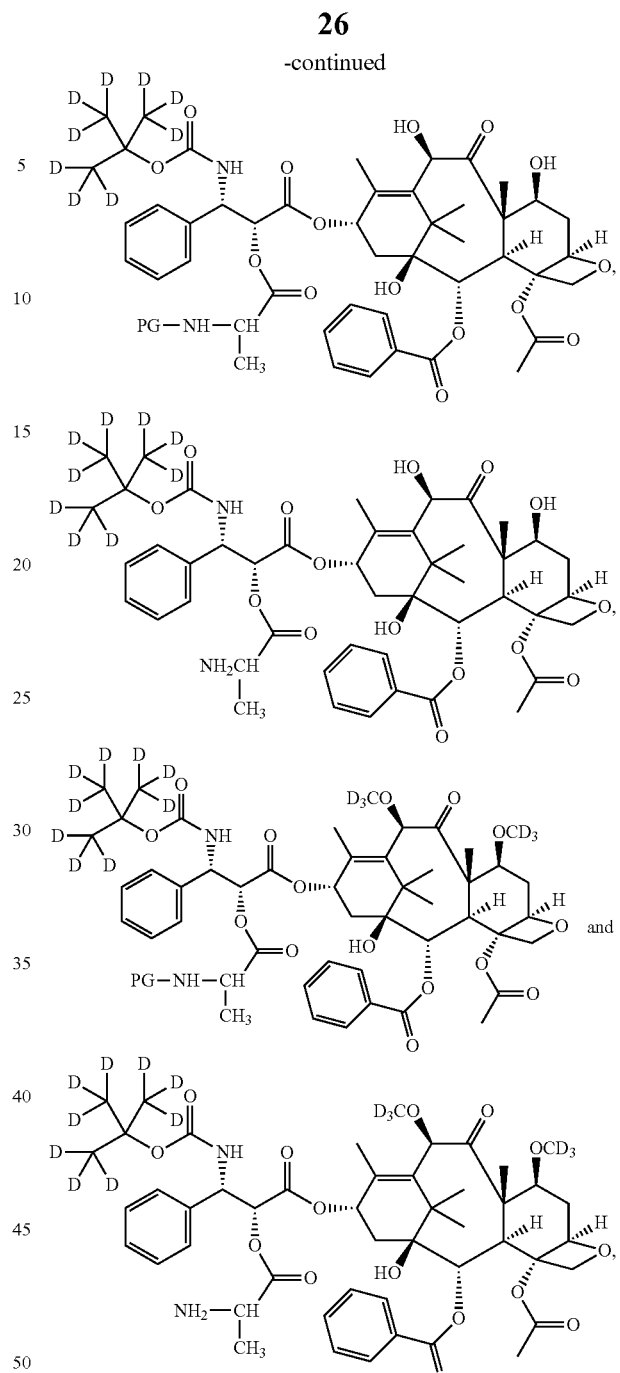

wherein PG is an amine protecting group, $R^1$ is selected from the group consisting of H, a hydroxy protecting group, a $C_{1-6}$, organic radical, and a deuterated/fluorinated $C_{1-6}$ organic radical (e.g., 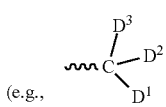

and each of $D^1$, $D^2$ and $D^3$ is independently selected from the group consisting of H, F, D and $CF_3$), and $R^2$ is selected from the group consisting of H, a hydroxy protecting group, a $C_{1-6}$ organic radical, and a deuterated/fluorinated $C_{1-6}$ organic radical

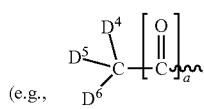

and (a) is either zero or one and each of $D^4$, $D^5$ and $D^6$ is independently selected from the group consisting of H, F, D and $CF_3$).

Compounds of Formula I are useful for a variety of purposes. For example, compounds of Formula I in which PG is H have an amine available for further functionalization (e.g., conjugation to a water soluble polymer). Similarly, compounds of Formula I in which PG is an amine protecting group can be deprotected to thereby provide a compound bearing an amine available for further functionalization (e.g., conjugation to a water-soluble polymer).

All articles, books, patents, patent publications and other publications referenced herein are incorporated by reference in their entireties. In the event of an inconsistency between the teachings of this specification and the art incorporated by reference, the meaning of the teachings in this specification shall prevail.

EXPERIMENTAL

It is to be understood that while the invention has been described in conjunction with certain preferred and specific embodiments, the foregoing description as well as the examples that follow are intended to illustrate and not limit the scope of the invention. Other aspects, advantages and modifications within the scope of the invention will be apparent to those skilled in the art to which the invention pertains.

One of ordinary skill in the art can make the compounds and carry out the methods described herein by reference to the relevant literature having regard for the present description and examples provided herein.

EXAMPLE 1

Preparation of 7β,10β-($D_6$)-Dimethoxydocetaxel-2'-Glycinate

Synthesis of 7β,10β-($D_6$)-Dimethoxy-10-Deacetylbaccatin III

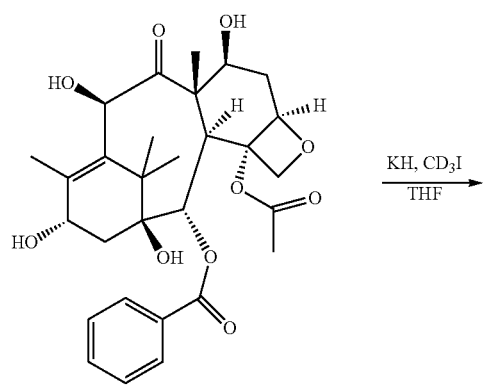

10-Deacetylbaccatin III

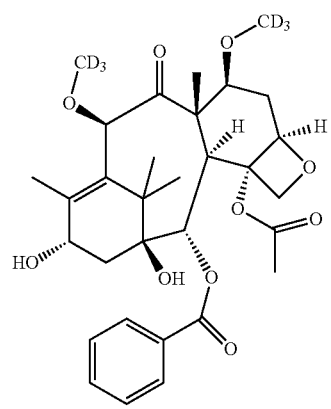

7β,10β-($D_6$)-Dimethoxy-10-Deacetylbaccatin III

A suspension of 10-deacetylbaccatin III (Sigma-Aldrich; 2.2 g) in tetrahydrofuran (25 ml) and a solution of methyl-($D_3$) iodide (9.5 g) in tetrahydrofuran (10 ml) was simultaneously added dropwise to a suspension of potassium hydride (5.0 g), in tetrahydrofuran (15 ml) at −20° C. Next the reaction mixture was stirred for eight hours at room temperature. Then, the reaction mixture was added to water (100 ml) and the resulting mixture was stored overnight at 4° C. Diisopropyl ether (100 ml) was added and the solid precipitate was filtered off. The crude product was purified by silica gel chromatography giving 0.75 g of the desired 7β,10β-($D_6$)-dimethoxy-10-deacetylbaccatin III having 98% purity as determined by HPLC analysis.

Synthesis of 7β,10β-($D_6$)-Dimethoxydocetaxel-2'Glycinate

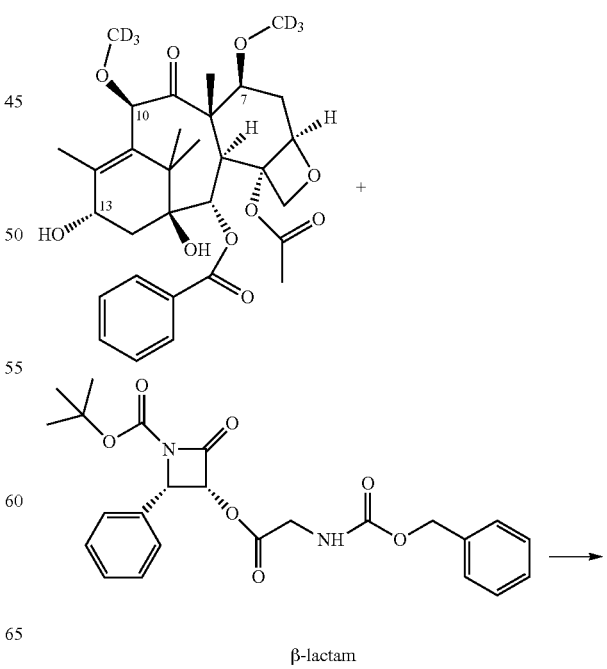

β-lactam

-continued

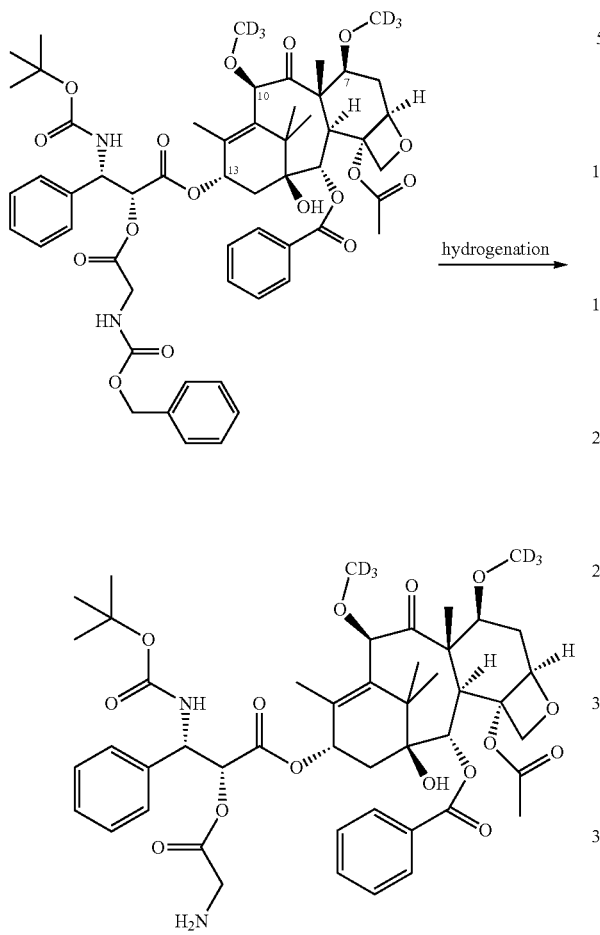

Dicyclohexylcarbodiimide (0.40 g) and then 4-(N,N-dimethylamino)pyridine (0.06 g) were added to a suspension of 7β,10β-($D_6$)-dimethoxy-10-deacetylbaccatin III (0.65 g), the β-lactam shown above (0.72 g), and powdered 4 A molecular sieves (0.15 g) in 6 ml of ethyl acetate. The mixture was stirred overnight at room temperature under an argon atmosphere, and was concentrated to dryness under reduced pressure. The resulting residue was purified by silica gel chromatography giving the corresponding 7β,10β-($D_6$)-dimethoxydocetaxel-2'-O—N-CBZ-glycinate in the form of a white solid (0.50 g).

The product was dissolved in 50 ml of anhydrous THF and 10% Pd/C (0.75 g) was added. The mixture was hydrogenated at 30 psi for three hours. Upon reaction completion, the mixture was filtered through a layer of celite which was subsequently washed with an additional amount of THF (50 mL). The desired product was obtained as a white solid after the solvent was removed under reduced pressure (0.42 g).

EXAMPLE 2

Preparation of 10β-($D_3$)-Methoxydocetaxel-2-O-Alaninate

Synthesis of 7β-Triethylsilyl-10-Deacetylbaccatin III

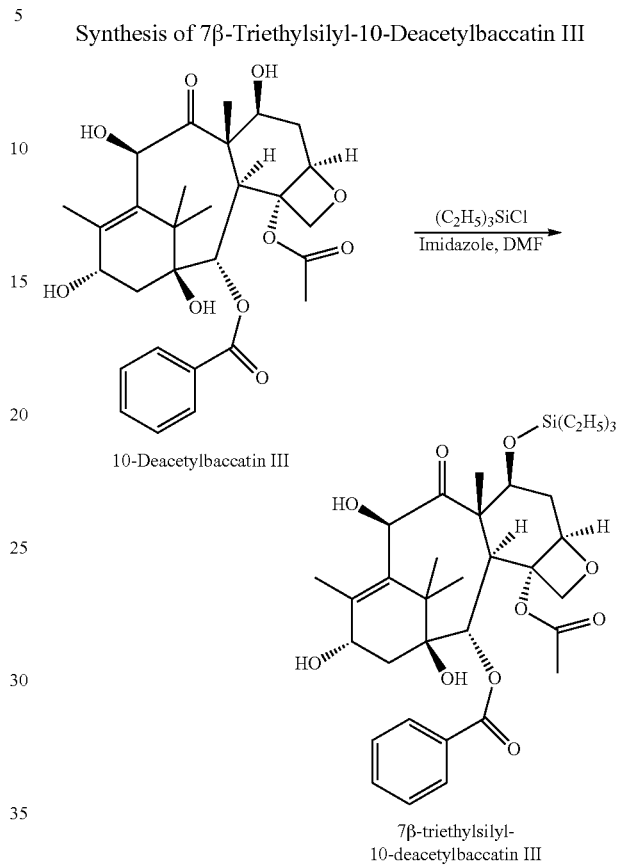

Chlorotriethylsilane (3.7 ml, 0.0221 mol) was added dropwise at 0° C. to a solution of 10-deacetylbaccatin III (3.00 g, 0.0056 mol) and imidazole (1.50 g, 0.0222 mmol) in 140 ml of N,N-dimethylformamide (DMF) and the reaction mixture was stirred for two hours at 0° C. Next, ethyl acetate was added and the obtained solution was washed with water, brine, dried with $MgSO_4$ and concentrated to dryness. The crude product was purified by silica gel chromatography using hexane:EtOAc=1:1 as an eluent to give 3.35 g of 7β-triethylsilyl-10-deacetylbaccatin III as a white solid.

Synthesis of 7β-Triethylsilyl,10β-($D_3$)-Methoxy-10-Deacetylbaccatin III

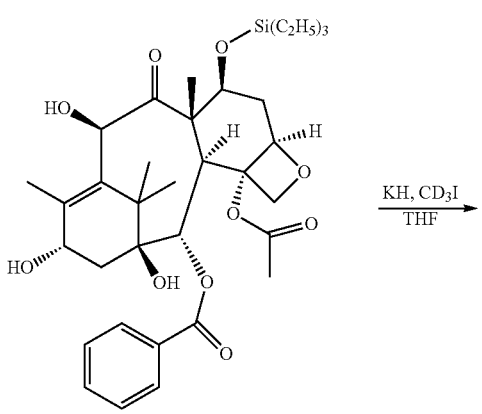

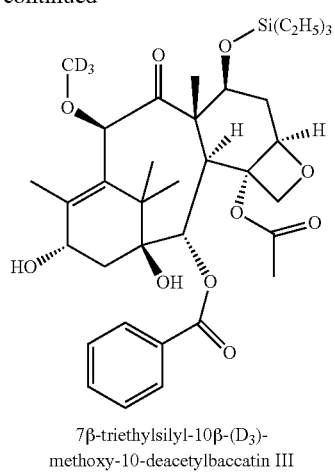

7β-triethylsilyl-10β-(D₃)-
methoxy-10-deacetylbaccatin III

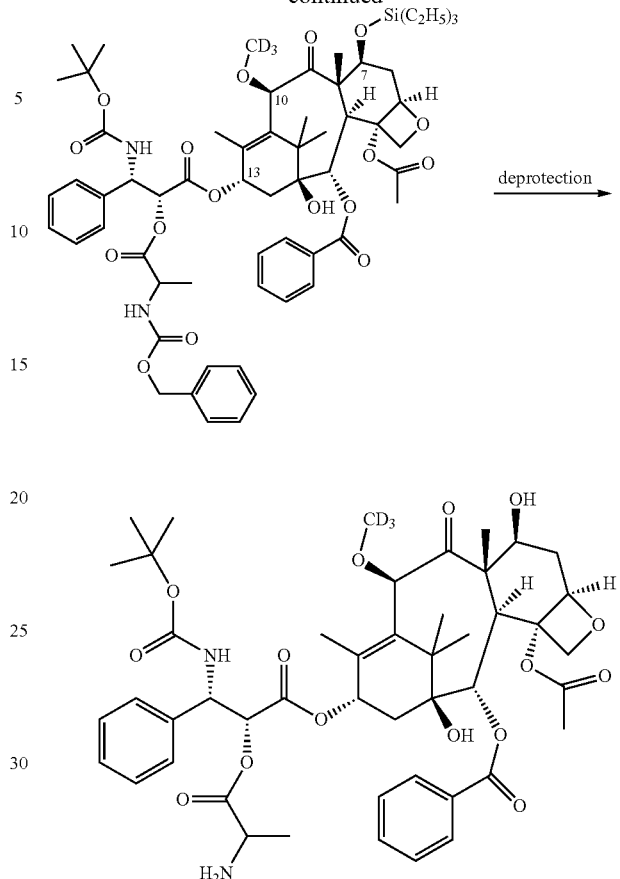

A suspension of 7β-triethylsilyl-10-deacetylbaccatin III (2.7 g) in tetrahydrofuran (25 ml) and a solution of methyl-(D₃) iodide (9.5 g) in tetrahydrofuran (10 ml) was simultaneously added dropwise to a suspension of potassium hydride (5.0 g) in tetrahydrofuran (15 ml) at −20° C. Next the reaction mixture was stirred for eight hours at room temperature. Then, the reaction mixture was added to water (100 ml) and the resulting mixture was stored overnight at 4° C. Diisopropyl ether (100 ml) was added and the solid precipitate was filtered off. The crude product was purified by silica gel chromatography giving 0.85 g of the desired 7β-triethylsilyl-10β-(D₃)-methoxy-10-deacetylbaccatin III having 97% purity as determined by HPLC analysis.

Synthesis of 10β-(D₃)-Methoxydocetaxel-2'-O-Alaninate

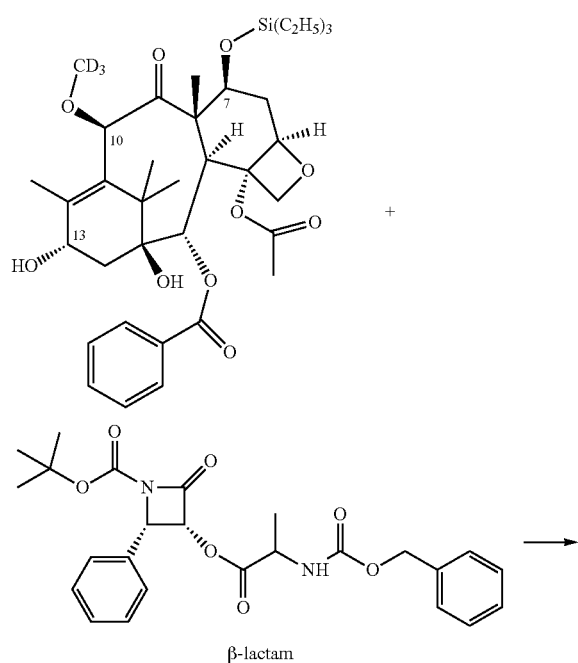

β-lactam

Dicyclohexylcarbodiimide (0.40 g) and then 4-(N,N-dimethylamino)pyridine (0.06 g) were added to a suspension of 7β-triethylsilyl,10β-(D₃)-methoxy-10-deacetylbaccatin III (0.80 g), β-lactam showed above (0.75 g), and powdered 4 A molecular sieves (0.15 g) in 6 ml of ethyl acetate. The mixture was stirred overnight at room temperature under an argon atmosphere, and was concentrated to dryness under reduced pressure. The resulting residue was purified by silica gel chromatography giving Z-7β-triethylsilyl-10β-(D₃)-methoxydocetaxel-2'-O—N-CBZ-alaninate in the form of a white solid (0.75 g).

The product was dissolved in 0.2N solution of hydrogen chloride in ethyl alcohol (40 ml) and stirred overnight at 0° C. under the nitrogen atmosphere. Next, the reaction mixture was diluted with distilled water (15 ml) and the product was extracted two times with dichloromethane (2×60 ml). The extract was dried (MgSO₄) and concentrated to dryness under reduced pressure. The residue was dissolved in 50 ml of anhydrous THF and 10% Pd/C (0.75 g) was added. The mixture was hydrogenated at 30 psi for three hours. Upon reaction completion, the mixture was filtered through a layer of celite which was subsequently washed with an additional amount of THF (50 mL). The solvent was distilled off under reduced pressure. The crude product was purified by silica gel chromatography giving 0.45 g of the desired 10β-(D₃)-methoxydocetaxel-2'-O-alaninate.

EXAMPLE 3

Preparation of Cabazitaxel-2'-O-Glycinate

Synthesis of 7β,10β-Dimethoxy-10-Deacetylbaccatin III

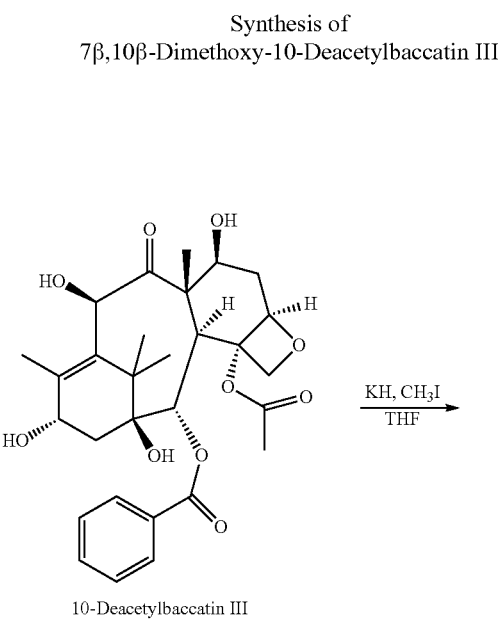

A suspension of 10-deacetylbaccatin III (Sigma-Aldrich; 4.4 g) in tetrahydrofuran (50 ml) and a solution of methyl iodide (20.5 g) in tetrahydrofuran (20 ml) was simultaneously added dropwise to a suspension of potassium hydride (10.0 g), in tetrahydrofuran (30 ml) at −20° C. Next the reaction mixture was stirred for eight hours at room temperature. Then, the reaction mixture was added to water (200 ml) and the resulting mixture was stored overnight at 4° C. Diisopropyl ether (200 ml) was added and the solid precipitate was filtered off. The crude product was purified by silica gel chromatography giving 1.55 g of the desired 7β,10β-dimethoxy-10-deacetylbaccatin III having 98% purity as determined by HPLC analysis.

Synthesis of Cabazitaxel-2'-O-Glycinate

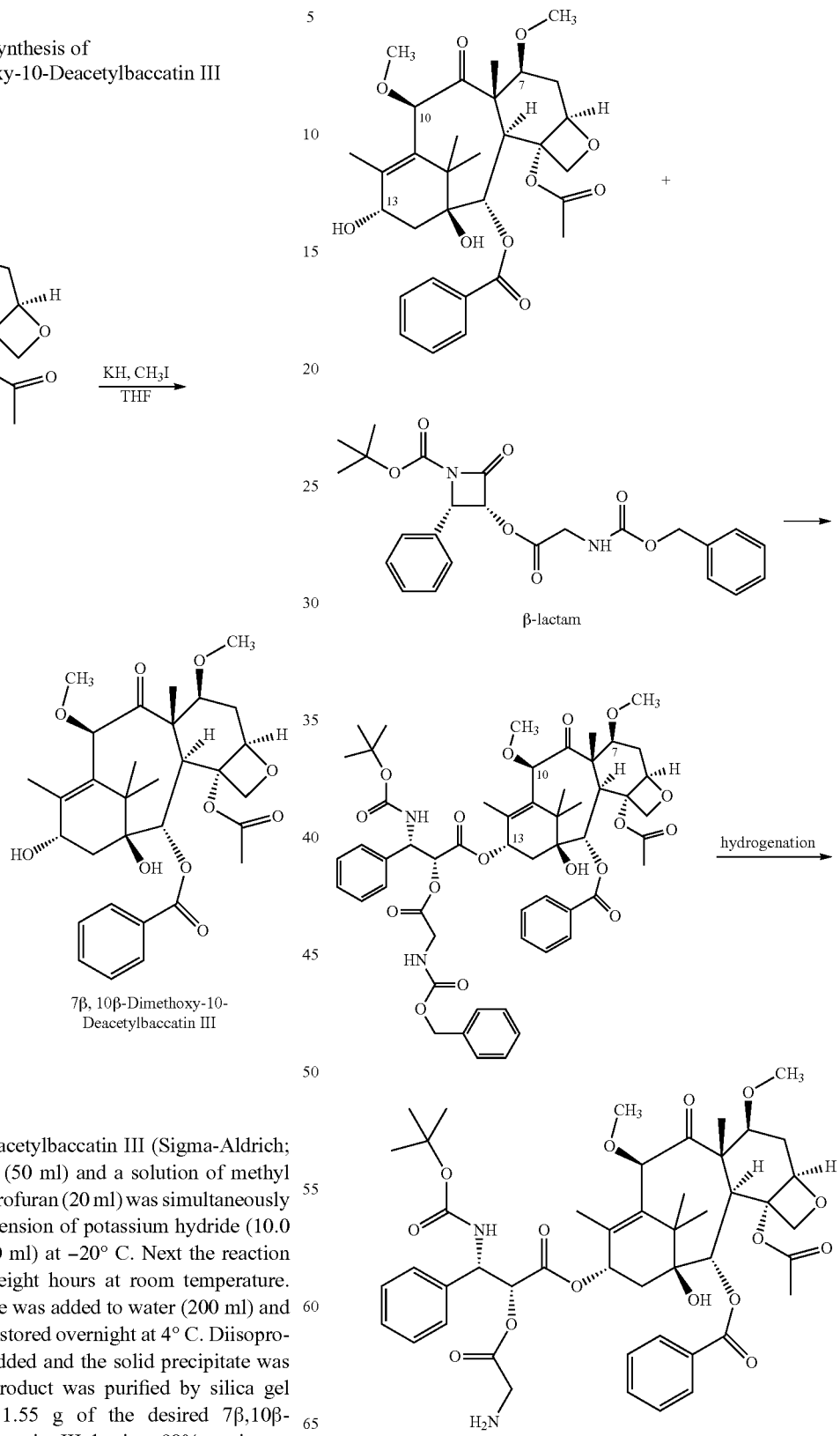

Dicyclohexylcarbodiimide (0.80 g) and then 4-(N,N-dimethylamino)pyridine (0.12 g) were added to a suspension of 7β,10β-dimethoxy-10-deacetylbaccatin III (1.35 g), β-lactam shown above (1.55 g), and powdered 4 A molecular sieves (0.35 g) in 15 ml of ethyl acetate. The mixture was stirred overnight at room temperature under an argon atmosphere, and was concentrated to dryness under reduced pressure. The resulting residue was purified by silica gel chromatography giving the corresponding Cabazitaxel-2'-O—N-CBZ-glycinate in the form of a white solid (1.05 g).

The product was dissolved in 100 ml of anhydrous THF and 10% Pd/C (1.50 g) was added. The mixture was hydrogenated at 30 psi for three hours. Upon reaction completion, the mixture was filtered through a layer of celite which was subsequently washed with an additional amount of THF (50 mL). The desired product was obtained as a white solid after the solvent was removed under reduced pressure (0.80 g).

What is claimed is:

1. A method comprising esterifying a baccatin III compound of Formula III, which compound is encompassed by the formula:

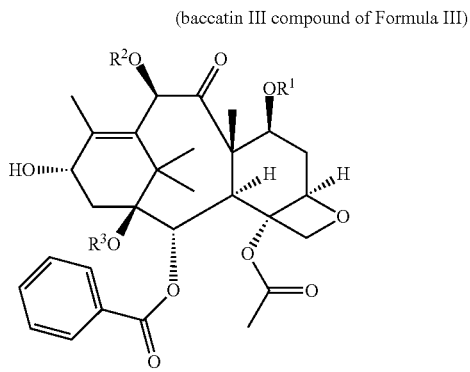

(baccatin III compound of Formula III)

wherein:
$R^1$ is selected from the group consisting of H, a hydroxy protecting group, a $C_{1-6}$ organic radical;
$R^2$ is selected from the group consisting of H, a hydroxy protecting group, a $C_{1-6}$ organic radical; and
$R^3$ is H or a hydroxy protecting group, with an ester linkage-providing compound of Formula II, which compound is encompassed by the formula:

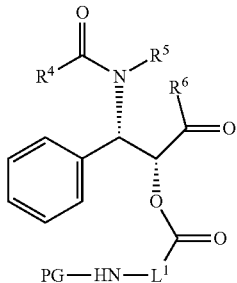

(Formula II)

wherein:
$R^4$ is $C_6H_5$— or

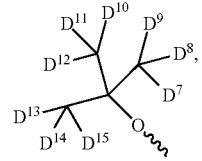

and each of $D^7, D^8, D^9, D^{10}, D^{11}, D^{12}, D^{13}, D^{14}$ and $D^{15}$ is independently selected from the group consisting of H, dueterium;
$L^1$ is alkylene having 1-10 carbon atoms;
PG is an amino protecting group; and
either: (i) $R^5$ is H and $R^6$ is —OH; or (ii) $R^5$ and $R^6$ represent a single covalent bond between the nitrogen to which $R^5$ is attached and the carbonyl carbon to which $R^6$ is attached.

2. The method of claim 1, wherein $R^1$ is selected from the group consisting of H, $CH_3$.

3. The method of claim 1, wherein $R^2$ is selected from the group consisting of H, $CH_3$, and $C(O)CH_3$.

4. The method of claim 1, wherein $R^3$ is H.

5. The method of claim 1, wherein $L^1$ is substituted alkyl having 1-10 carbon atoms.

6. The method of claim 1, wherein PG is selected from the group consisting of carbobenzyloxy, p-methoxybenzyl carbonyl, tert-butyloxycarbonyl, 9-fluorenylmethyloxycarbonyl, acetyl, benzoyl, benzyl, p-methoxybenzyl, 3,4dimethoxybenzyl, p-methoxyphenyl and a sulfonamide.

7. The method of claim 1, wherein $R^5$ is H and $R^6$ is OH.

8. The method of claim 1, wherein $R^5$ and $R^6$ represent a single covalent bond.

* * * * *